(12) United States Patent
Tribe et al.

(10) Patent No.: US 7,635,349 B2
(45) Date of Patent: Dec. 22, 2009

(54) SYRINGE PUMPS

(75) Inventors: Robert James Tribe, Loughton (GB); Chris Pickles, Abbots Langley (GB)

(73) Assignee: Smiths Group PLC, London (GB)

( * ) Notice: Subject to any disclaimer, the term of this patent is extended or adjusted under 35 U.S.C. 154(b) by 849 days.

(21) Appl. No.: 09/920,728

(22) Filed: Aug. 3, 2001

(65) Prior Publication Data

US 2003/0205587 A1    Nov. 6, 2003

(30) Foreign Application Priority Data

Aug. 16, 2000    (GB) .................... 0020060.0

(51) Int. Cl.
*A61M 31/00* (2006.01)
*A61M 37/00* (2006.01)
*A61M 1/00* (2006.01)

(52) U.S. Cl. .................. 604/131; 604/152; 604/500

(58) Field of Classification Search ............... 604/500, 604/30, 31, 36, 38, 118, 65–67, 121, 131, 604/154, 134–135, 151, 152, 155, 187, 207–211, 604/218, 224, 228, 245, 246; 222/390, 258, 222/46–48, 309–311; 128/DIG. 12, DIG. 13; 417/326, 18

See application file for complete search history.

(56) References Cited

U.S. PATENT DOCUMENTS

| | | | | |
|---|---|---|---|---|
| 4,137,913 | A | * | 2/1979 | Georgi ............... 128/DIG. 12 |
| 4,562,571 | A | * | 12/1985 | Deman et al. ............... 370/202 |
| 4,678,408 | A | * | 7/1987 | Nason et al. ................. 417/410 |
| 4,952,205 | A | | 8/1990 | Mauerer et al. |
| 5,232,449 | A | * | 8/1993 | Stern et al. .................. 604/154 |
| 5,244,461 | A | | 9/1993 | Derlien |
| 5,647,853 | A | * | 7/1997 | Feldmann et al. ........... 604/155 |
| 5,800,387 | A | * | 9/1998 | Duffy et al. ................... 604/65 |
| 5,827,223 | A | | 10/1998 | Butterfield |
| 6,179,569 | B1 | * | 1/2001 | Kojima et al. ............... 417/415 |
| 6,248,093 | B1 | * | 6/2001 | Moberg ....................... 604/131 |
| 6,362,591 | B1 | * | 3/2002 | Moberg ....................... 318/685 |
| 6,423,035 | B1 | * | 7/2002 | Das et al. .................... 604/155 |
| 6,485,465 | B2 | * | 11/2002 | Moberg et al. .............. 604/154 |
| 6,551,277 | B1 | * | 4/2003 | Ford ........................... 604/131 |

FOREIGN PATENT DOCUMENTS

EP    0 354 852 A2    2/1990

(Continued)

OTHER PUBLICATIONS

Brochure: Asena GH made by Alaris Medical Systems.

*Primary Examiner*—Matthew F Desanto
(74) *Attorney, Agent, or Firm*—Louis Woo

(57) ABSTRACT

A syringe pump has a motor rotating a leadscrew, which drives a plunger head retainer to push a plunger along the barrel of a syringe so as to dispense medication to a patient. A force sensor in the head retainer measures the force on the plunger to detect when there is an occlusion restricting flow of medication. When an excess force is detected an alarm is generated and the motor is reversed to reduce the force to about 10% of that at which the occlusion is detected. The occlusion can be removed with a reduced risk of a bolus of medication being dispensed after which the user restarts the pump so that the plunger is driven normally.

9 Claims, 1 Drawing Sheet

FOREIGN PATENT DOCUMENTS

| | | |
|---|---|---|
| EP | 1066846 A1 | 1/2001 |
| EP | 1110569 A2 | 6/2001 |
| GB | 2 352 637 * | 2/2001 |
| WO | WO 98/57694 | 12/1998 |
| WO | WO 01/37904 A2 | 5/2001 |

* cited by examiner

SYRINGE PUMPS

BACKGROUND OF THE INVENTION

This invention relates to syringe pumps.

Syringe pumps are used to supply medication to a patient from a pre-filled syringe via an infusion line. The syringe pump applies a force to the plunger of the syringe to drive medication into the infusion line at a controlled rate. It is common to have some provision to detect occlusion to flow of liquid out of the pump, such as caused by kinked tubing, and to respond to this by stopping the pump and sounding an alarm. The occlusion may be detected by measuring the force exerted on the plunger head by the pump driver, to detect excessive force. As described in GB2352637, the plunger head retainer itself may include a force sensor. The excess force produced until the occlusion is detected is accommodated by deformation of the elastic components, such as the fluid tubing and the syringe plunger head. When the pump is stopped, therefore, the medication fluid upstream of the occlusion is subject to compressive forces. When the occlusion is cleared, such as by straightening kinked tubing, the compressive force may cause a bolus of medication to flow to the patient. This can, in some situations, present a hazard to the patient.

WO97/07843 describes a peristaltic pump where the pump is reversed on detection of a possible occlusion and is then driven forwardly again before generating an alarm.

BRIEF SUMMARY OF THE INVENTION

It is an object of the present invention to provide an alternative syringe pump and method of operation.

According to one aspect of the present invention there is provided a syringe pump adapted to receive a syringe of the kind having a plunger movable along a barrel, the pump including means for detecting an occlusion to flow of medication from the syringe, the pump being operable in response to a detected occlusion to reverse the drive applied to move the plunger along the barrel sufficiently to reduce excess force on the medication caused by the occlusion.

The means for detecting occlusion preferably includes a force sensor and the pump may be arranged to reverse the drive until force detected by the force sensor reaches a predetermined level, such as substantially 10% of the force at which the occlusion is detected.

According to a second aspect of the present invention there is provided a method of controlling a syringe pump including the steps of applying a force to drive a plunger along a barrel of a syringe to dispense medication, detecting an occlusion to the flow of medication out of the syringe, and responding to a detected occlusion by reversing the drive on the plunger sufficient to reduce excess pressure on the medication.

According to a third aspect of the present invention there is provided a method of controlling a syringe pump including the steps of applying a force to drive a plunger along a barrel of a syringe to dispense medication, detecting force on the plunger, and responding to a force on the plunger above a predetermined value by changing the force applied to drive the plunger such that the detected force reduces below the predetermined value.

The force applied to drive the plunger is preferably changed to reduce the detected force to substantially 10% of the predetermined value. The pump may be arranged to generate an alarm when force on the plunger exceeds a predetermined value. The pump is preferably arranged to reapply force to dispense medication only when the pump is manually restarted after detection of an occlusion.

A syringe pump and its method of operation, according to the present invention, will now be described, by way of example, with reference to the accompanying drawing.

DETAILED DESCRIPTION OF THE PREFERRED EMBODIMENT

Figure 1:
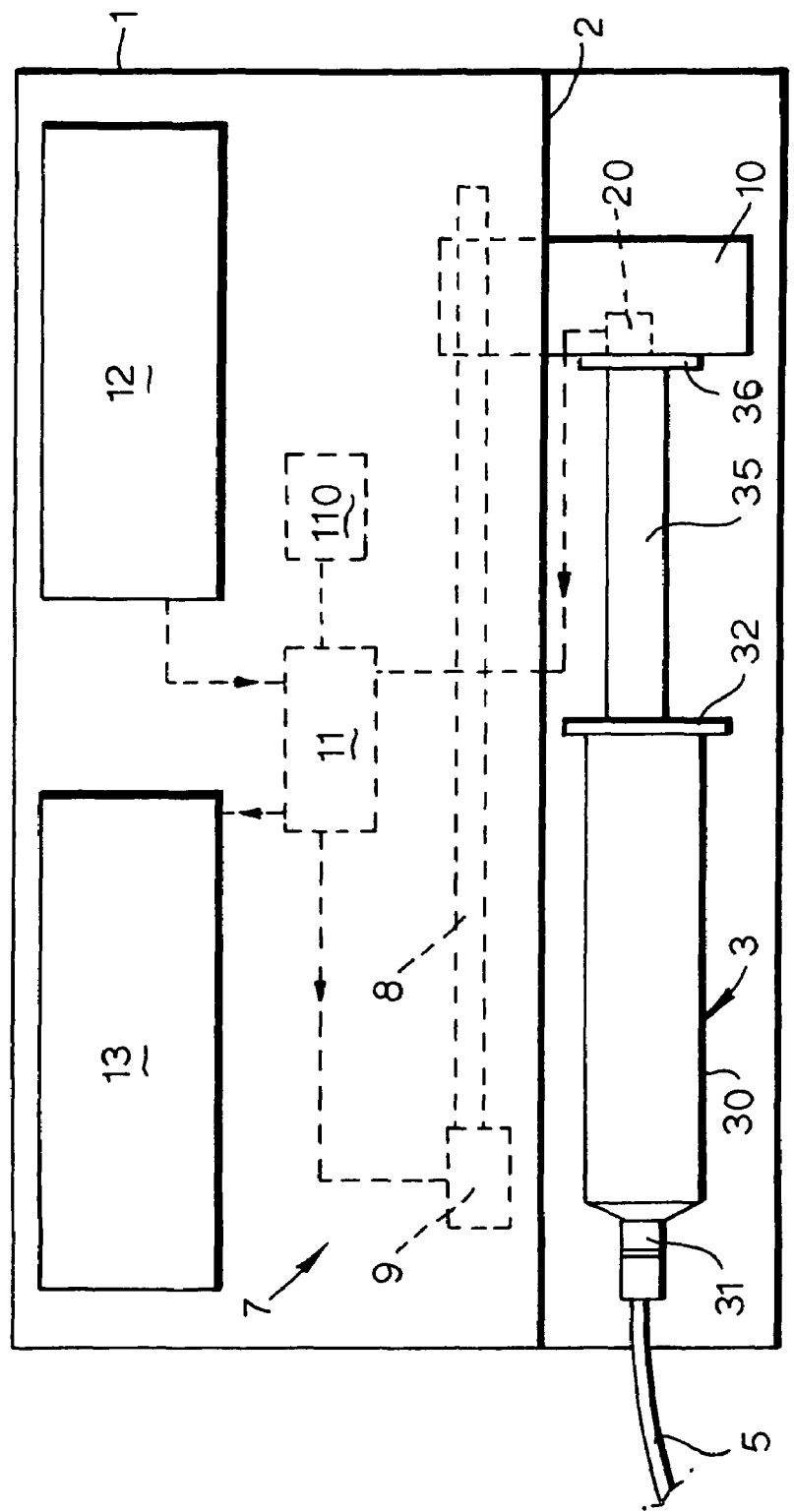
FIG. 1 is a simplified view of the front of the pump.

The pump includes an outer housing 1 with a recess 2 on its front surface shaped to receive a syringe 3 of conventional kind. The syringe 3 has a cylindrical barrel 30 with an outlet or nose 31 at its forward end and a flange or ear 32 at its rear end. The nose 31 is connected to an infusion line 5 so that a medication liquid in the syringe 3 can be dispensed to a patient via the infusion line, by pushing in the plunger 35. The pump has a drive mechanism 7, including a lead screw 8 driven by an electric motor 9. A retainer mechanism 10 is movable along the lead screw as it rotates and engages the head 36 of the plunger 35, so as to move the plunger along the barrel 30. The motor 9 is driven by a control unit 11, which receives inputs from a keypad 12, or other user input means, and various sensors. The control unit 11 also provides an output to a display 13.

The plunger head retainer 10 includes a force sensor 20, as described in greater detail in GB2352637, which responds to the force exerted on the plunger head 36 by the retainer and provides an output to the control unit 11. The control unit 11 includes a memory 110 containing information as to an upper, maximum predetermined value of force $F_{max}$. If this force is exceeded, it indicates an obstruction to forward movement of the plunger, which is usually caused by an occlusion in the path of medication from the syringe. The force sensor thereby operates as an occlusion detector. Most commonly, such an occlusion would be caused by a kink in the infusion line 5 but it could be caused, for example, by inadvertent use of a clamp on the tubing or by a blood clot where the medication enters the patient.

The control unit 11 compares the output from the sensor 20 with the contents of the memory 110 and, if the force exceeds $F_{max}$, it provides an alarm signal, such as an audible alarm and a warning indication on the display panel 13. The control unit 11 also stops forward drive by the motor 9 and applies signals to drive the motor in reverse until the force detected by the sensor 20 reduces to some level above zero, typically about 10% of $F_{max}$. At the same time, when this reduced level of force is detected, the control unit 11 stops drive to the motor 9 until the user clears the occlusion and manually restarts the pump. The force applied to the medication is considerably reduced compared with what it would be if the motor had been simply stopped on detection of the occlusion. Thus, when the occlusion is removed, such as by straightening kinked tubing, there will be no significant bolus of medication dispensed to the patient. The force on the plunger is preferably maintained slightly above zero in order to ensure that there is no reverse flow of medication along the infusion line when the occlusion is removed.

What we claim is:

1. A syringe pump adapted to receive a syringe having a plunger movable along a barrel, the pump comprising: a drive mechanism for moving said plunger along said barrel; and an occlusion detector responsive to occlusion to flow of medication from said syringe, said occlusion detector including a force sensor that directly senses the force exerted on the plunger in response to occlusion to flow of medication from said syringe, wherein the pump is operable in response to a detected occlusion to reverse the drive applied to move said plunger along said barrel sufficiently until the force detected by said force sensor falls by a predetermined amount.

2. A pump according to claim 1, wherein the pump is arranged to reverse the drive until force detected by said force sensor is substantially 10% of the force at which an occlusion is detected.

3. A syringe pump adapted to receive a syringe having a plunger movable along a barrel, the pump comprising: a drive mechanism, said drive mechanism including a motor, a leadscrew driven by said motor and a plunger retainer movable along the leadscrew such as to move said plunger along said barrel; and a force sensor mounted with said plunger retainer to directly detect excess force on said plunger, wherein the pump is operable in response to an output from said force sensor indicative of an excess force to reverse said motor until the output of said force sensor indicates an absence of an excessive force on said plunger.

4. A method of controlling a syringe pump comprising the steps of: applying a force to drive a plunger in a forward movement along a barrel of a syringe to dispense medication; directly detecting force on said plunger; responding to a force on said plunger above a predetermined value by changing the direction of force applied to drive said plunger in reverse such that said directly detected force reduces below said predetermined value.

5. A method according to claim 4, wherein force applied to drive said plunger is changed to reduce said detected force to substantially 10% of said predetermined value.

6. A method according to claim 4, wherein the pump generates an alarm when force on said plunger exceeds a predetermined value.

7. A method according to claim 4, wherein the pump only reapplies force to dispense medication when the pump is manually restarted after detection of an occlusion.

8. A syringe pump adapted to receive a syringe having a plunger movable along a barrel, comprising: a drive mechanism for moving said plunger along said barrel; an occlusion detector responsive to occlusion to flow of medication from said syringe, said occlusion detector including a force sensor that directly senses the force exerted on the plunger in response to occlusion to flow of medication from said syringe, a control unit and a memory, wherein said control unit compares the force sensed by said force sensor with contents of said memory to determine if the sensed force exceeds a $F_{max}$, and wherein if the sensed force does exceed $F_{max}$, said control unit sends out signals to cause said drive mechanism to stop and then reverse its drive movement until the force sensed by said force sensor is reduced to some level above zero.

9. A syringe pump according to claim 8, wherein said drive mechanism is arranged to reverse its drive movement until the force detected by said force sensor is approximately 10% of $F_{max}$, said control unit stopping said drive mechanism at that time.

* * * * *